United States Patent
Ross et al.

(10) Patent No.: US 10,743,917 B2
(45) Date of Patent: Aug. 18, 2020

(54) WALKING SKATES SYSTEM REMOVABLY COUPLED TO AN EXTERNAL RING FIXATION SYSTEM

(71) Applicant: Orthofix S.R.L., Bussolengo (IT)

(72) Inventors: John D. Ross, Ovilla, TX (US); Mikhail L. Samchukov, Coppell, TX (US); Alexander M. Cherkashin, Flower Mound, TX (US); Andrea Ottoboni, Rovigo (IT); Andrea Zaccaria, Tregnago (IT); Stephen Vincent Blake, Allen, TX (US)

(73) Assignees: ORTHOFIX S.R.L., Bussolengo, Verona (IT); TEXAS SCOTTISH RITE HOSPITAL FOR CHILDREN, Dallas, TX (US)

( * ) Notice: Subject to any disclaimer, the term of this patent is extended or adjusted under 35 U.S.C. 154(b) by 0 days.

(21) Appl. No.: 15/764,784

(22) PCT Filed: Sep. 19, 2016

(86) PCT No.: PCT/EP2016/072098
§ 371 (c)(1),
(2) Date: Mar. 29, 2018

(87) PCT Pub. No.: WO2017/055116
PCT Pub. Date: Apr. 6, 2017

(65) Prior Publication Data
US 2018/0310962 A1    Nov. 1, 2018

(30) Foreign Application Priority Data

Sep. 29, 2015 (EP) .................................... 15425075

(51) Int. Cl.
*A61B 17/62* (2006.01)
*A61B 17/64* (2006.01)

(52) U.S. Cl.
CPC .......... *A61B 17/62* (2013.01); *A61B 17/6425* (2013.01); *A61B 17/6441* (2013.01)

(58) Field of Classification Search
CPC .. A61B 17/62; A61B 17/6425; A61B 17/6441
(Continued)

(56) References Cited

U.S. PATENT DOCUMENTS 3,727,610 A * 4/1973 Riniker .............. A61B 17/6441
606/56
4,360,012 A * 11/1982 McHarrie .......... A61B 17/6441
606/54

(Continued)

FOREIGN PATENT DOCUMENTS

GB       2519650 A      4/2015

OTHER PUBLICATIONS

International Search Report and Written Opinion of the International Searching Authority dated Jan. 2, 2017 in connection with International Application No. PCT/EP2016/072098, 8 pages.

*Primary Examiner* — Pedro Philogene
*Assistant Examiner* — David C Comstock
(74) *Attorney, Agent, or Firm* — Haynes and Boone, LLP

(57) ABSTRACT

Walking skates system removably coupled underneath a bottom half-ring of an external ring fixation system comprising a pair of skates, each skate of the pair of skates having a curved bottom profile from which a protruding connection body provided with at least one slot projects, the system further comprising a connecting member having a first end configured to be connected to an opening in the bottom half-ring of the external ring fixation system and a second end provided with a hole for connection to the slot in the connection body of the skate.

23 Claims, 4 Drawing Sheets

(58) Field of Classification Search
USPC .................................. 606/54, 55, 56; 623/29
See application file for complete search history.

(56) References Cited

U.S. PATENT DOCUMENTS

| | | | | |
|---|---|---|---|---|
| 5,152,280 A | * | 10/1992 | Danieli | .............. A61B 17/6458 |
| | | | | 606/54 |
| 2012/0029516 A1 | * | 2/2012 | Taylor | .................... A61B 17/62 |
| | | | | 606/56 |
| 2012/0041439 A1 | * | 2/2012 | Singh | ...................... A61B 17/62 |
| | | | | 606/54 |
| 2012/0232554 A1 | * | 9/2012 | Shaevitz | .............. A61B 17/171 |
| | | | | 606/56 |
| 2013/0204248 A1 | | 8/2013 | Singh et al. | |
| 2016/0256194 A1 | * | 9/2016 | Wong | .................. A61B 17/171 |

* cited by examiner

WALKING SKATES SYSTEM REMOVABLY COUPLED TO AN EXTERNAL RING FIXATION SYSTEM

CROSS-REFERENCE TO RELATED APPLICATION(S)

The present application claims priority under 35 U.S.C. 365 to International Patent Application No. PCT/EP2016/072098 filed Sep. 19, 2016, entitled "WALKING SKATES SYSTEM REMOVABLY COUPLED TO AN EXTERNAL RING FIXATION SYSTEM", and through International Patent Application No. PCT/EP2016/072098, to European Patent Application No. 15425075.7 filed Sep. 29, 2015, each of which are incorporated herein by reference into the present disclosure as if fully set forth herein.

FIELD OF THE DISCLOSURE

The present disclosure is applicable to the sector of orthopaedics and relates to a system of walking skates which can be removably coupled underneath a bottom half-ring of an external ring fixation system so as to allow the patient to walk without resting their feet on the walking surface.

BACKGROUND

In order to allow the movement of patients to whom an external ring fixation system has been fixed, walking skates are normally associated underneath a bottom half-ring, namely the ring placed further downwards, close to the foot, said skates allowing the patient to walk normally without however touching the walking surface, so as to facilitate healing.

The document EP 2 777 565 A describes an external fixation system which uses such type of skates.

One problem which may arise with these types of skates systems is that they are often made in a personalized manner so as to assist as far as possible the walking movement which is to be obtained.

Should, instead, a standard type of skates system be used, it would not ensure the same walking comfort for all the patients.

Moreover, these systems have means for performing coupling to the bottom half-ring which often result in having to use predetermined fixing points, thus not offering the possibility of obtaining a degree of flexibility during assembly.

Last but not least, assembly of these known systems may prove to be difficult for the persons working in the sector.

Another known embodiment is disclosed in the US patent application No. US 2013/204248 A1 wherein a walking skates system is coupled underneath a bottom half ring of an external fixation system comprising a pair of skates each having a curved bottom profile.

However, this embodiment does not provide a plurality of fixing points for the skates on the half ring to which they are fixed and does not ensure flexibility of use for the patient.

A technical problem underlying the present disclosure is, therefore, that of providing a system of skates which can be removably coupled underneath a bottom half-ring of an external ring fixation system, able to provide a plurality of fixing points for the skates on the half-ring to which they are fixed, ensuring flexibility of use for the patients and at the same time easy manoeuvrability for the persons working in the sector during assembly thereof, so as to be easy to fit also for less expert persons, within the framework of a simple and rational constructional solution.

SUMMARY

The aforementioned technical problem is solved by a system of walking skates that is structured to be removably coupled underneath a bottom half-ring of an external ring fixation system comprising a pair of skates, each skate of said pair of skates having a curved bottom profile from which a protruding connection body provided with at least one slot projects, characterized in that said system further comprises a connecting member having a first end configured to be connected to an opening in the bottom half-ring of the external ring fixation system and a second end provided with a hole for connection to said slot in the connection body of the skate.

Advantageously, said protruding connection body of the skate extends over a length substantially equal to the length of the said skate.

Moreover, said protruding connection body of the skate has a base with a curved profile substantially parallel to the curved profile of the said skate and two projecting members or portions protruding from the curved base and spaced from each other.

In a preferred embodiment the two projecting members have a size different from each other.

The enclosed dependent claims describe preferred and particularly advantageous embodiments, in accordance with the present disclosure.

Further characteristic features and advantages will emerge more clearly from the detailed description provided hereinbelow of a preferred, but not exclusive embodiment of the present disclosure, with reference to the attached figures, provided by way of a non-limiting example.

DETAILED DESCRIPTION

Figure 1:
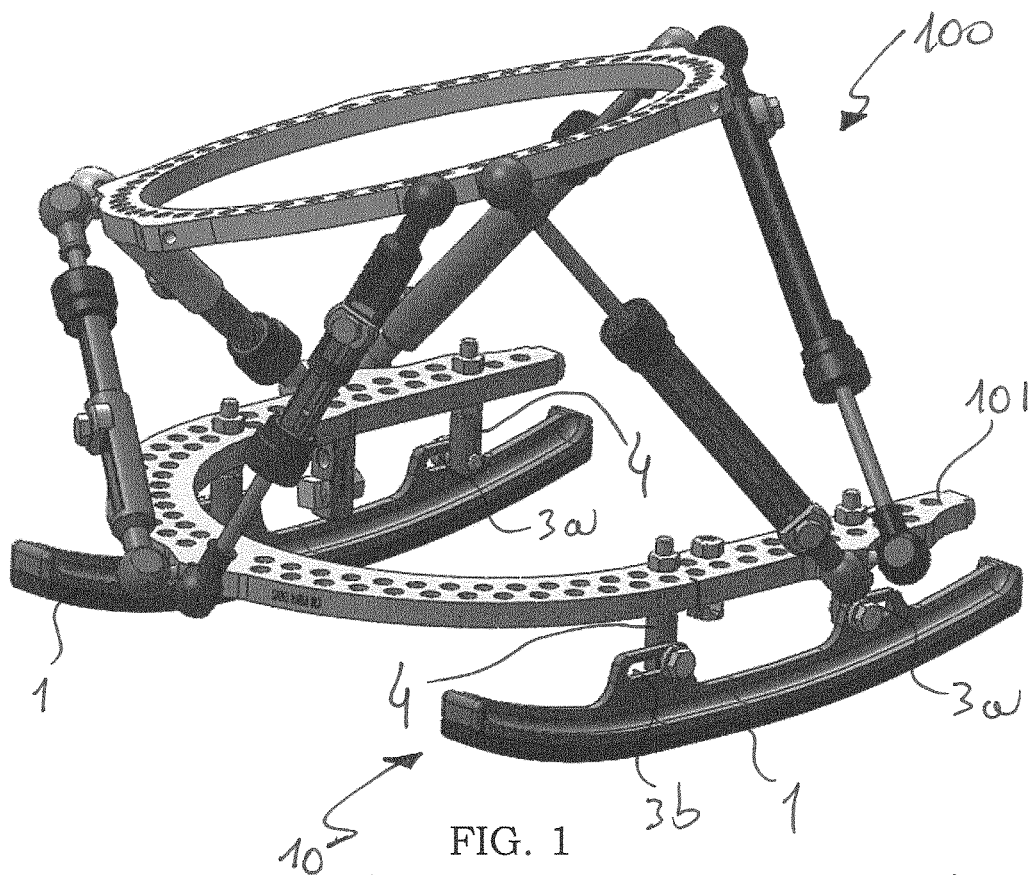
FIG. 1 shows a perspective view of a ring fixation system to the bottom half-ring of which a system of removable walking skates in accordance with the present disclosure are fixed.
Figure 2:
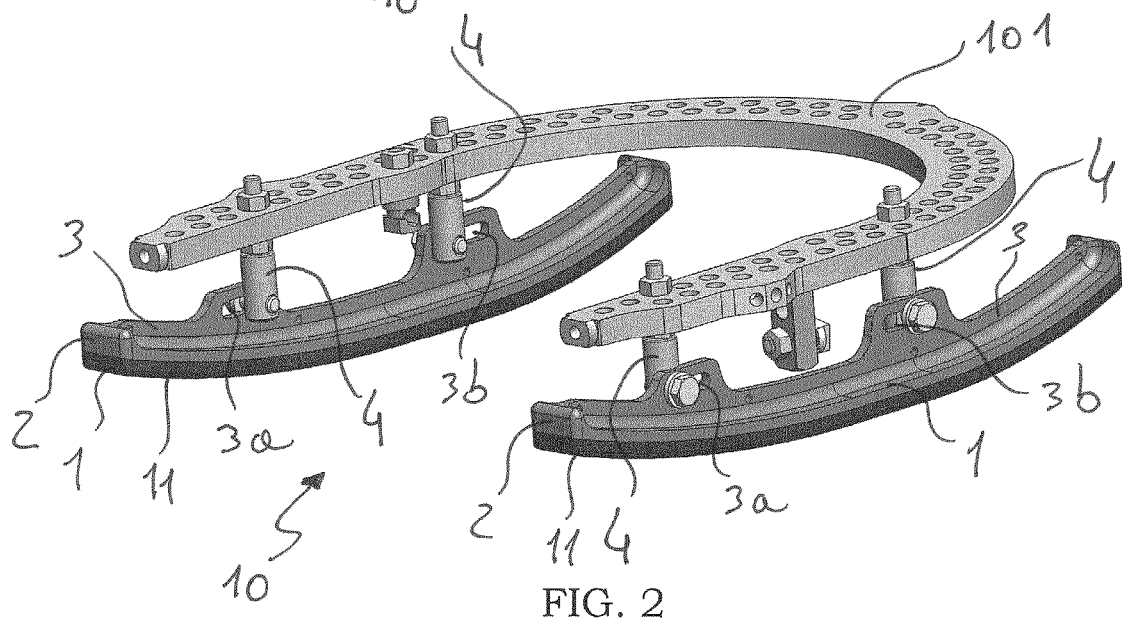
FIG. 2 shows a perspective view of only the bottom half-ring with the skates system according to FIG. 1.
Figure 3:
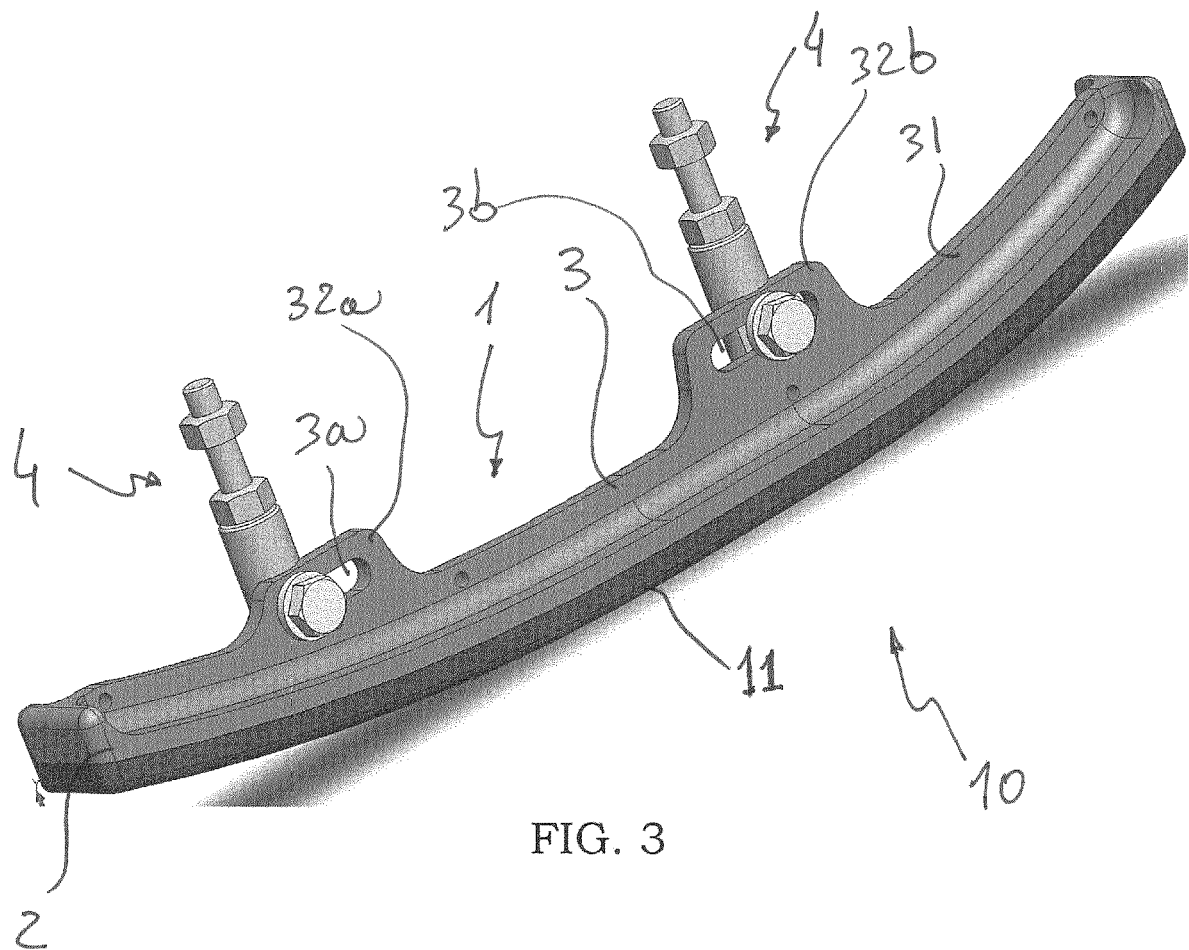
FIG. 3 shows perspective view of a skates system in accordance with the present disclosure.
Figure 4A:
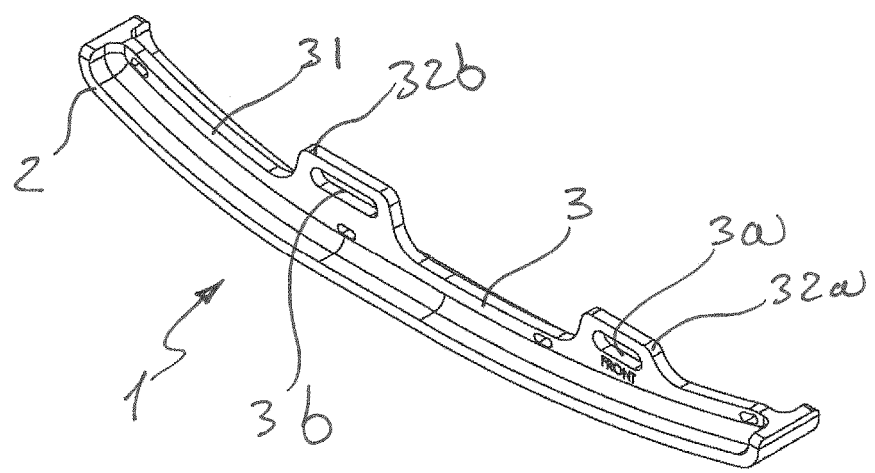
FIGS. 4A-4C show, respectively, a perspective, front and top view of a skate of the skates system according to the present disclosure.
Figure 4B:
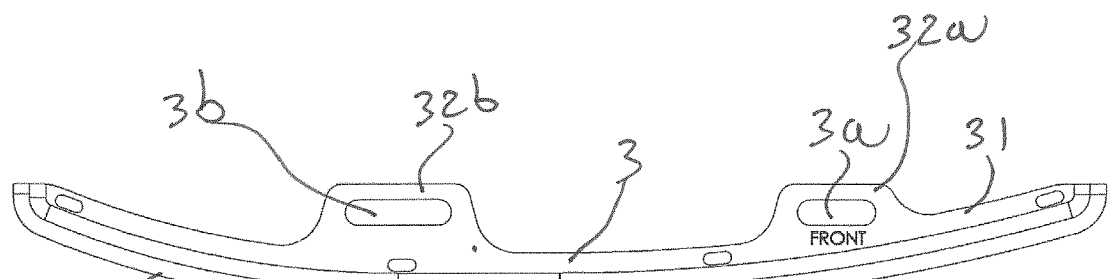
Figure 4C:
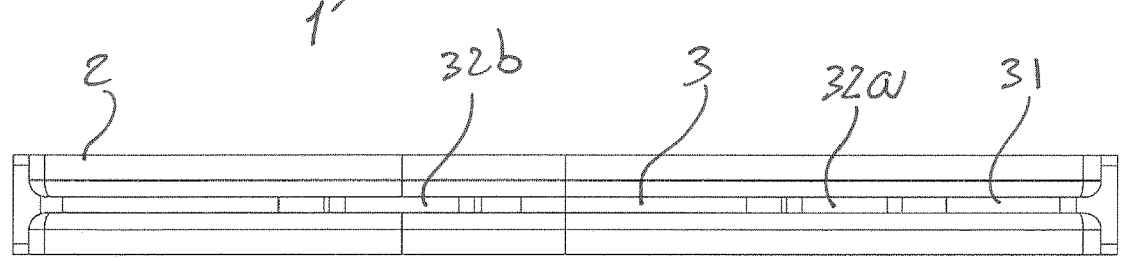

With reference to the attached figures and in particular to FIGS. 1-3, the reference number 10 indicates a skates system according to the present disclosure which can be removably fixed to an external ring fixation system 100, the latter being shown in FIG. 1 alone.

The skates system 10 comprises a pair of skates 1 which are identical to each other and therefore only one of them will be described in detail.

The skate 1 according to the present disclosure has a bottom profile 2 which is curved with a curvature formed in accordance with the technology of the sector.

A protruding connection body 3, in the example arranged centrally, projects from the bottom profile 2 of the skate 1 and extends over a length substantially equal to that of the skate 1 itself.

Basically, the protruding connection body 3 forms a kind of fin, the thickness of which in the example is equal to about ⅙th of the width of the skate 1, understood as being measured transversely with respect to the longitudinal extension of the skate 1.

Two slots 3a and 3b are formed in the protruding connection body 3.

Figure 5:
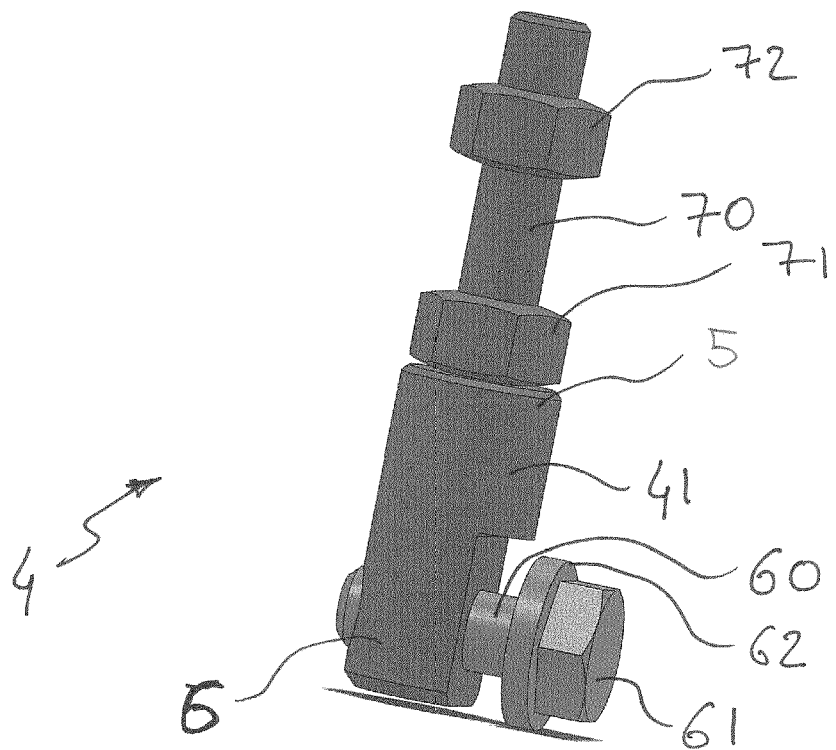
FIG. 5 shows a connecting member for connecting the skate shown in FIG. 4 to the half-ring.
Figures 6A, 6B:
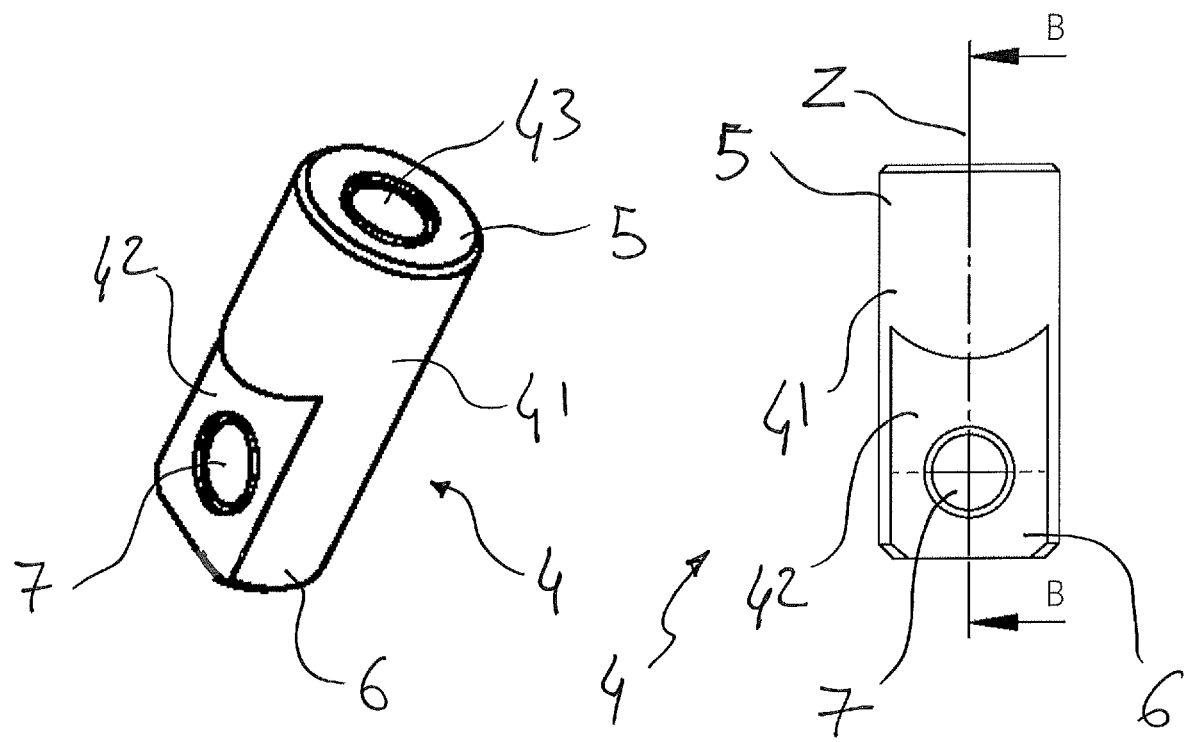
FIGS. 6A-6C show, respectively, a perspective, front and cross-sectional view along the line B-B of FIG. 6B of a detail of the connecting member shown in FIG. 5.
Figure 6C:
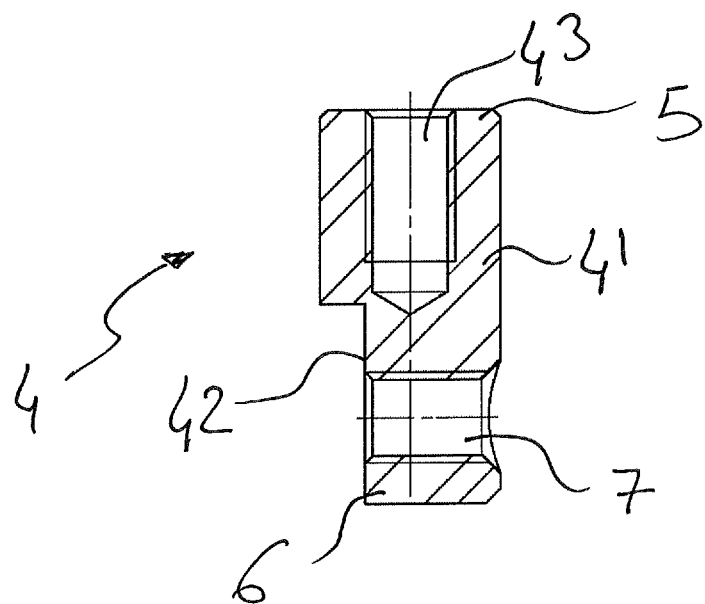

In accordance with the present disclosure, the system 10 further comprises at least one connecting member 4, shown in FIGS. 5 and 6, having a first end 5 configured to be connected to an opening in the bottom half-ring 101 of the external fixation system 100 and a second end 6 provided with a hole 7 for connection to the slot 3a, 3b in the connection body 3 of the skate 1.

In the example shown in the figures, the protruding connection body 3 of the skate 1 has a base 31 with a curved profile substantially parallel to the curved profile of the skate 1 itself and two projecting members or portions 32a, 32b protruding from the curved base 31 and spaced from each other.

Each of the two projecting members 32a, 32b comprises one of the two slots 3a, 3b.

In the example shown, each of said slots 3a, 3b has a longitudinal extension which is parallel to a surface on which the skates 1 rest.

In other words, the slots 3a, 3b which are oblong, longitudinally do not follow the curved profile of the skate, but are horizontally straight.

The two slots 3a, 3b have dimensions which are different from each other; more specifically, the slot 3a which will be arranged in the front of the skate 1, with respect to the walking direction, has a longitudinal extension smaller than that of the other slot 3b which will be arranged at the rear. For example, the longitudinal extension of the front slot 3a is equal to about 13 mm, while the longitudinal extension of the slot at the rear 3b is equal to about 20 mm, in a skate with a length of about 270 mm measured along a flat surface.

In addition, preferably the two projecting members 32a, 32b are arranged at a different distance from the respective closest end of the skate 1.

More particularly, the projecting member 32a, which could be defined as the front part, is placed closer to the front end of the skate 1 compared to the distance between the other projecting member 32b and the rear-lying end of the skate 1.

In other words, there is a front projecting member 32a and a rear projecting member 32b, the front member being placed closer to the front end of the skate than the rear member to the other rear end of the said skate.

Essentially, the two projecting members 32a, 32b, and consequently the respective slots 3a, 3b, are not arranged symmetrically with respect to a transverse central plane of the skate.

With reference to the connecting member 4, it comprises a cylindrical body 41 which extends along a longitudinal axis Z and has a through hole 7 arranged transversely with respect to the longitudinal axis Z of the cylindrical body 41 so as to be able to receive a screw 60 for fixing to the skate 1.

The cylindrical body 41 also has a removed portion around the hole 7 so as to create a flat wall 42 abutting against the protruding connection body 3, more precisely abutting against the projecting members 32a, 32b. This flat wall 42 is arranged parallel to the longitudinal axis Z of the cylindrical body 41.

The cylindrical body 41 also has a blind hole 43 at the opposite end 5 to the through-hole 7, this blind hole 43 extending along the longitudinal axis Z of the cylindrical body 41 so as to be able to receive a fixing screw 70 for coupling to the bottom side of the half-ring 101 of the external ring fixation system 100.

As is known in the field, the bottom portion of the skate 1 is preferably provided with a tread 11 for dampening the impact of the walking steps.

Operationally speaking, in order to fix the skate 1 to the bottom half-ring 101, the skate is arranged so that the front end is arranged at the front with respect to the walking direction. A first connecting member 4 is connected to one of the two slots 3a, 3b by means of screwing of the screw 60 which will suitably have an operating head 61.

A washer 62, which may be formed integrally with the screw 60 attached to the head 61, is suitably arranged between the operating head 61 of the screw 60 and the projecting members 32a, 32b of the protruding connection body 3.

Since the slot 3a, 32b extends over a certain length, the exact point for fixing the connecting member 4 to the skate will be chosen depending on the greater ergonomics which can be perceived by the patient who is using the ring fixation system.

Fixing the connecting member 4 to the half-ring 101 is performed by means of the other screw 70 which is screwed onto the half-ring 101 and passes inside the blind hole 43. Locking nuts 71 and 72 may be suitably engaged. A first nut 71 is arranged between the connecting member 4 and the half-ring 101, while the other nut 72 is arranged at the end of the screw 70 which passes through the bottom half-ring 101 and bears against the bottom half-ring 101.

As can be understood from the above description, the skates system according to the present disclosure is able to meet the goals and overcome the drawbacks mentioned above in the introductory part of the present disclosure.

Obviously a person skilled in the art, in order to satisfy any specific requirements which might arise, may make numerous modifications and variations to the present disclosure, all of which are contained moreover within the scope of protection of the present disclosure, as defined by the following claims.

What is claimed is:

1. A walking skates system removably coupled underneath a bottom half-ring of an external ring fixation system, comprising:
   a pair of skates, each skate having a curved bottom profile;
   a protruding connection body formed in each skate on an opposite side from the curved bottom profile;
   at least one slot in the protruding connection body of each skate;
   at least one connecting member associated with each skate having a first end configured to be connected to an opening in the bottom half-ring of the external ring fixation system and a second end configured to be connected to the at least one slot of the connection body of the skate; and
   at least one hole in the at least one connecting member.

2. The skates system according to claim 1, wherein the protruding connection body of the skate extends over a length substantially equal to the length of the skate.

3. The skates system according to claim 1, wherein the protruding connection body of the skate has a base with a curved profile substantially parallel to the curved profile of the skate and two projecting portions protruding from the curved base and spaced from each other.

4. The skates system according to claim 3, wherein each of the two projecting portions has a respective elongated slot.

5. The skates system according to claim 4, wherein the slots of the two projecting portions have a size different from each other.

6. The skates system according to claim 4, wherein the slots of the two projecting portions have a longitudinal extension which is parallel to a surface on which the skates rest.

7. The skates system according to claim 1, wherein the protruding connection body of the skate is placed in the central portion of the skate.

8. The skates system according to claim 1, wherein the at least one connecting member comprises a cylindrical body which extends along a longitudinal axis and has a through-hole placed at the second end arranged transversely with respect to the longitudinal axis of the cylindrical body, so as to be able to receive a screw for fixing to the skate.

9. The skates system according to claim 8, wherein the cylindrical body has a reduced diameter portion around the through-hole so as to create flat wall abutting against the protruding connection body, the flat wall being arranged parallel to the longitudinal axis of the cylindrical body.

10. The skates system according to claim 9, wherein the cylindrical body has a blind hole at the opposite end to the through-hole, the blind hole extending along the longitudinal axis of the cylindrical body to receive a fixing screw for coupling to the bottom side of the half-ring of the external ring fixation system.

11. The skates system according to claim 1, wherein the curved bottom profile has an anterior portion having a first radius, a posterior portion having a second radius, and a central portion between the anterior portion and the posterior portion, the central portion having a third radius, the third radius being different than the first radius and the second radius.

12. The skates system of claim 11, wherein the third radius is greater than the first radius and the second radius.

13. The skates system of claim 1, wherein a central portion of the curved bottom profile is substantially flat, and an anterior portion and a posterior portion of the curved bottom profile are both curved.

14. A walking skates system structured to be removably coupled underneath a bottom half-ring of an external ring fixation system and comprising:
 a pair of skates, each skate having a tread with a curved bottom profile;
 a protruding connection body formed in each skate and provided with at least one slot, the protruding connection body having a transverse width less than a transverse width of the tread; and
 at least one connecting member for each skate having a first end configured to be connected to an opening in the bottom half-ring of the external ring fixation system and a second end configured to be connected to the at least one slot in the connection body of the skate.

15. The skates system according to claim 14, wherein the protruding connection body of the skate extends over a length substantially equal to the length of the skate.

16. The skates system according to claim 14, wherein the protruding connection body of the skate has a base with a curved profile substantially parallel to the curved profile of the skate and two projecting members protruding from the curved base and spaced from each other.

17. The skates system according to claim 16, wherein each of the two projecting members has a respective elongated slot.

18. The skates system according to claim 17, wherein the slots of the two projecting members have a size different from each other.

19. The skates system according to claim 17, wherein the slots of the two projecting members have a longitudinal extension which is substantially parallel to a surface on which the skates rest.

20. The skates system according to claim 14, wherein the protruding connection body of the skate is placed in the central portion of the skate.

21. The skates system according to claim 14, wherein the at least one connecting member comprises a cylindrical body which extends along a longitudinal axis and has a through-hole located at the second end and arranged transversely with respect to the longitudinal axis of the cylindrical body to be able to receive a pin or screw for fixing to the at least one slot of the skate.

22. The skates system according to claim 21, wherein cylindrical body has a reduced diameter portion around the through-hole so as to create a flat wall abutting against the protruding connection body, and wherein the flat wall is arranged parallel to the longitudinal axis of the cylindrical body.

23. A walking skates system removably coupled underneath a bottom half-ring of an external ring fixation system, comprising:
 a pair of skates, each skate having a curved bottom profile;
 a protruding connection body formed in each skate protruding in a direction opposite the curved bottom profile;
 at least one slot in the protruding connection body;
 at least one connecting member having a first end configured to be removably connected to an opening in the bottom half-ring of the external ring fixation system and a second end configured to be removably connected to the at least one slot of the connection body of the skate; and
 a through-hole located at the second end and arranged to be able to receive a pin or screw for fixing the at least one connecting member to the at least one slot.

* * * * *